(12) United States Patent
Spreen

(10) Patent No.: US 10,758,531 B2
(45) Date of Patent: Sep. 1, 2020

(54) REGIMENS AND COMPOSITIONS FOR TREATING HIV INFECTIONS AND AIDS

(71) Applicant: ViiV Healthcare Company, Wilmington, DE (US)

(72) Inventor: William R. Spreen, Research Triangle Park, NC (US)

(73) Assignee: ViiV Healthcare Company, Wilmington, DE (US)

(*) Notice: Subject to any disclaimer, the term of this patent is extended or adjusted under 35 U.S.C. 154(b) by 0 days.

(21) Appl. No.: 16/308,844

(22) PCT Filed: Jun. 30, 2017

(86) PCT No.: PCT/US2017/040182
§ 371 (c)(1),
(2) Date: Dec. 11, 2018

(87) PCT Pub. No.: WO2018/005914
PCT Pub. Date: Jan. 4, 2018

(65) Prior Publication Data
US 2019/0142828 A1      May 16, 2019

Related U.S. Application Data

(60) Provisional application No. 62/357,458, filed on Jul. 1, 2016.

(51) Int. Cl.
| | | |
|---|---|---|
| *A61K 31/69* | (2006.01) | |
| *A61K 31/4985* | (2006.01) | |
| *A61K 31/505* | (2006.01) | |
| *A61P 31/12* | (2006.01) | |
| *A61K 31/7068* | (2006.01) | |
| *A61K 31/553* | (2006.01) | |
| *A61K 31/675* | (2006.01) | |
| *A61P 31/18* | (2006.01) | |
| *A61K 9/00* | (2006.01) | |

(52) U.S. Cl.
CPC ........ *A61K 31/4985* (2013.01); *A61K 9/0053* (2013.01); *A61K 31/505* (2013.01); *A61K 31/553* (2013.01); *A61K 31/675* (2013.01); *A61K 31/7068* (2013.01); *A61P 31/12* (2018.01); *A61P 31/18* (2018.01)

(58) Field of Classification Search
CPC .... C07D 249/10; C07D 405/12; A61K 31/69; A61K 38/07
See application file for complete search history.

(56) References Cited

U.S. PATENT DOCUMENTS

2017/0114048 A1    4/2017   Cihlar et al.

FOREIGN PATENT DOCUMENTS

WO     WO2017/064628 A1    4/2017

OTHER PUBLICATIONS

Janssen R&D Ireland Ltd., Janssen Collaborates with ViiV Healthcare to Develop Two-Drug single tablet regimen for the maintenance treatment of people living with HIV, 10 pages, Jun. 12, 2014.*
Gilead Sciences, Inc., Gilead presents preliminary data on Bictegravir, an Investigational integrase strand transfer inhibitor for the treatment of HIV, 2 pages, Jun. 20, 2016.*
Janssen R&D Ireland Ltd., Janssen collaborates with ViiV Healthcare to Develop two-drug single tablet regimen for the maintenance treatment of People living with HIV. http//www.prnewswire.com/new-releases/janssen-colaborates-with-viiv-healthcare-to-develop-two-drug-single-tablet-regimen-for-the-mainenance-treatment-of-people-living-with-hiv-262843591.html#, Jun. 12, 2014, p. 1, ln 2-4, 7-9, 19-21, p. 2, 6, 11, 13.
Gilead Science, Inc., Gilead Presents Preliminary Data on Bictegravir, an Investigational Integrase Strand Transfer Inhibitor for the Treatment of HIV, Jun. 20, 2016, http//www.gilead.com/news/press-releases/2016/gilead-presents-preliminary-data-on-bictegravir-an-investigational-integrase-strand-transfer-inhibitor-for-the-treatment-of-hiv.

* cited by examiner

*Primary Examiner* — Deepak R Rao
(74) *Attorney, Agent, or Firm* — Craig T. Ajmo

(57) ABSTRACT

Methods for treating HIV or AIDS in a human are provided using two drug regimens comprising a bictegravir and rilpivirine, as well as compositions containing such compounds.

12 Claims, No Drawings

US 10,758,531 B2

REGIMENS AND COMPOSITIONS FOR TREATING HIV INFECTIONS AND AIDS

FIELD OF THE INVENTION

Disclosed are methods for treating or preventing human immunodeficiency virus or AIDS in a human using a combination comprising bictegravir and rilpivirine, as well as compositions comprising bictegravir and rilpivirine.

BACKGROUND OF THE INVENTION

Human immunodeficiency virus ("HIV") infection and related diseases are a major public health problem worldwide. Human immunodeficiency virus type 1 ("HIV-1") encodes three enzymes that are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al., *N. Engl. J. Med.* (1998) 338:853-860; Richman, *Nature* (2001) 410:995-1001).

A goal of antiretroviral therapy is to achieve viral suppression in an HIV-infected human. Treatment guidelines published by the United States Department of Health and Human Services provide that achievement of viral suppression requires the use of combination therapies, i.e., several drugs from at least two or more drug classes. (PANEL ON ANTIRETROVIRAL GUIDELINES FOR ADULTS AND ADOLESCENTS: GUIDELINES FOR THE USE OF ANTIRETROVIRAL AGENTS IN HIV-1-INFECTED ADULTS AND ADOLESCENTS. Department of Health and Human Services. Available at http://aidsinfo.nih.gov/ContentFiles/AdultandAdolescentGL.pdf. Section accessed Apr. 19, 2017.)

A number of reviews of clinical data involving large patient populations have established that a viral load decreases following antiretroviral therapy ("ART") initiation and that decrease correlates with a reduced risk of AIDS progression or death. (Murray J S, Elashoff M R, Iacono-Connors L C, Cvetkovich T A, Struble K A. The use of plasma HIV RNA as a study endpoint in efficacy trials of antiretroviral drugs. *AIDS.* 1999;13(7):797-804; Marschner I C, Collier A C, Coombs R W, et al. Use of changes in plasma levels of human immunodeficiency virus type 1 RNA to assess the clinical benefit of antiretroviral therapy. *J Infect Dis.* 1998; 177(1):40-47; and, Thiebaut R, Morlat P, Jacqmin-Gadda H, et al, with the Groupe d'Epidemiologie du SIDA en Aquitaine (GECSA); Clinical progression of HIV-1 infection according to the viral response during the first year of antiretroviral treatment. *AIDS.* 2000;14(8):971-978.) In light of these findings, viral load testing may be used as a surrogate marker of a positive treatment response. (Human immunodeficiency virus type 1 RNA level and CD4 count as prognostic markers and surrogate end points: a meta-analysis. HIV Surrogate Marker Collaborative Group. *AIDS Res Hum Retroviruses.* 2000; 16(12):1123-1133.) A statistically significant change in viral load is a three-fold change, which equates to a 0.5 $\log_{10}$ copies/mL change. Depending on the study or assay used, viral suppression in general is defined as a viral load below the level of detection, which is an HIV RNA copy number of less than 20 to 75 copies/mL. (Damond F, Roquebert B, Benard A, et al. Human immunodeficiency virus type 1 (HIV-1) plasma load discrepancies between the Roche COBAS AMPLICOR HIV-1 MONITOR Version 1.5 and the Roche COBAS AmpliPrep/COBAS TaqMan HIV-1 assays. *J Clin Microbiol.* 2007; 45(10):3436-3438.)

More than 25 antiretroviral (ARV) drugs in 6 mechanistic classes are Food and Drug Administration (FDA)-approved for treatment of HIV infection. These 6 classes include the nucleoside/nucleotide reverse transcriptase inhibitors (NRTIs), non-nucleoside reverse transcriptase inhibitors (NNRTIs), protease inhibitors (PIs), a fusion inhibitor (FI), a CCR5 antagonist, and integrase strand transfer inhibitors (INSTIs). In addition, two drugs, ritonavir (RTV or r) and cobicistat (COBI or c) are used solely as pharmacokinetic (PK) enhancers (ie, boosters) to improve the PK profiles of some ARV drugs (e.g., PIs and the INSTI elvitegravir [EVG]).

A standard course of care for a patient infected with HIV is to treat them with a combination of three or more antiviral agents. The initial ARV regimen for a treatment-naive patient generally consists of two different NRTIs, targeting HIV reverse transcriptase (a "backbone") usually abacavir/lamivudine (ABC/3TC), tenofovir alafenamide/emtricitabine (TAF/FTC), or tenofovir disoproxil fumarate/emtricitabine (TDF/FTC) one or more agents active against one or more different HIV targets, such as an HIV protease inhibitor ("PI") or an HIV integrase inhibitor. For certain patients infected with HIV or diagnosed with AIDS there is an unmet medical need to two treat them with fewer antiviral agents. There are a number of reasons for giving fewer anti-HIV drugs.

For one, long-term use of certain antiretroviral drugs, particularly nucleoside reverse transcriptase inhibitors can lead to treatment-associated toxicities. Further, historical experience with HIV infected patients shows that many of them are now living longer. This population shows many typical age-related comorbidities, including renal disease, cardiovascular disease, liver disease, cognitive decline, diabetes, dyslipidemia, and osteoporosis, among others. Drug-sparing approaches would be beneficial for this aging population. (McCutchan J A, Wu J W, Robertson K, Koletar S L, Ellis R J, Cohn S, et al. (2007) HIV suppression by HAART preserves cognitive function in advanced, immune-reconstituted AIDS patients. *AIDS* 21: 1109-1117; Salter M L, Lau B, Go V F, Mehta S H, Kirk G D (2011) HIV infection, immune suppression, and uncontrolled viremia are associated with increased multimorbidity among aging injection drug users. *Clin. Infect. Dis.* 53: 1256-1264.) These comorbidities can be exacerbated by drug-related adverse events from long-term antiretroviral use. (Cunningham J, Sprague S M, Cannata-Andia J, Coco M, Cohen-Solal M, Fitzpatrick L, et al. (2004) Osteoporosis in chronic kidney disease. *Am J Kidney Dis* 43: 566-571; Sabin C A, Worm S W, Weber R, Reiss P, El-Sadr W, Dabis F, et al. (2008) Use of nucleoside reverse transcriptase inhibitors and risk of myocardial infarction in HIV-infected patients enrolled in the D:A:D study: a multi-cohort collaboration. *Lancet* 371: 1417-1426).

These varied problems have led to attempts to try dual antiretovital therapies, but studies have revealed a higher risk of treatment failure compared triple therapy regimens. (Havlir D V, Marschner I C, Hirsch M S, Collier A C, Tebas P, Bassett R L, et al. (1998) Maintenance antiretroviral therapies in HIV infected patients with undetectable plasma HIV RNA after triple-drug therapy. AIDS Clinical Trials Group Study 343 Team. *N Engl J Med* 339: 1261-1268; Pialoux G, Raffi F, Brun-Vezinet F, Meiffredy V, Flandre P, Gastaut J A, et al. (1998); A randomized trial of three maintenance regimens given after three months of induction therapy with zidovudine, lamivudine, and indinavir in previously untreated HIV-1-infected patients. Trilege (Agence Nationale de Recherches sur le SIDA 072) Study Team. *N Engl J Med* 339: 1269-1276; Reijers M H, Weverling G J, Jurriaans S, Wit F W, Weigel H M, Ten Kate R W, et al. (1998); Maintenance therapy after quadruple induction therapy in HIV-1 infected individuals: Amsterdam Duration of Antiretroviral Medication (ADAM) study. *Lancet* 352: 185-190.).

Although different combinations of antiretroviral drugs have been developed for the treatment of HIV and AIDS, a need still exists for additional treatment regimens tailored to patient needs, such as safe and effective two drug antiretroviral regimens.

DEFINITIONS

The following terms in quotations used herein have the following meanings.

"About" means within the margins of statistical error of a measure used in the field, art, or subject matter it refers or relates to.

"ART-experienced" or "antiretroviral therapy-experienced" means with regards to a human, one currently being treated or recently treated with one or more antiviral agents used to treat HIV or AIDS.

"Combination of the Invention" means a combination of bictegravir or a pharmaceutically acceptable salt or form thereof and rilpivirine or a pharmaceutically acceptable salt or form thereof.

"Composition(s) of the invention" means a composition(s) containing only two antiviral agents, those being bictegravir or a pharmaceutically acceptable salt or form thereof and rilpivirine or a pharmaceutically acceptable salt or form thereof, but which composition may comprise other components but excluding an additional antiretroviral agent. The antiviral agents may be in separate compositions or together in one composition.

"For example," "an example," "such as," and "e.g." may be used interchangeably and mean to point to or relate to non-exhaustive examples.

"HIV" or "human immunodeficiency virus" each means HIV-1 or HIV-2, or any mutant, group, clinical isolate, subtype, or clade thereof.

"Patient" means human.

"Regimen(s) of the invention" means a regimen(s) comprising an aspect of administration, formulation, route of administration, dose, dosing interval, and treatment duration using only two antiviral agents, those being bictegravir or a pharmaceutically acceptable salt or form thereof and rilpivirine or a pharmaceutically acceptable salt or form thereof, but which regimen may comprise or use other components but excluding an antiretroviral agent.

"Virologically suppressed" means detecting an HIV ribonucleic acid (RNA) copy number of less than a given number of copies per milliliter (mL) using a TaqMan 2.0 assay (Roche Diagnostics, Indianapolis, Ind., USA).

The symbol "↓" means to lower a dosage or frequency of dosing.

The symbol "↑" means to raise a dosage or frequency of dosing.

The symbol "↔" means to keep a dosage and frequency of dosing the same.

SUMMARY OF THE INVENTION

In one embodiment, this invention comprises a method of treating a patient infected with a human immunodeficiency virus using a combination of the invention, composition of the invention or using a regimen of the invention.

In another embodiment of the method the patient is virologically suppressed, such as having an HIV copy number of less than between 0 and 200 copies per mL, 20 copies per mL, 50 copies per mL, 100 copies per mL, or 200 copies per mL.

In another embodiment, the human immunodeficiency virus in a patient is not resistant to either antiretroviral component of a combination of the invention, or only partially resistant to either or both of the antiretroviral component(s), or resistant to an integrase inhibitor, such as elvitegravir or raltegravir.

In certain embodiments a method of treatment comprises the two antiviral agents of a combination of the invention, or composition of the invention each taken once daily. They make be taken at the same time in one composition or separate compositions, or when in separate formulations may be taken at different times of the day.

In still other embodiments the combination or composition for use in the method comprises a pharmaceutically acceptable form of bictegravir such as bictegravir sodium or other pharmaceutically acceptable salt equivalent to between about 40 mg. and 200 mg. of bictegravir and a pharmaceutically acceptable form of rilpivirine such as rilpivirine hydrochloride equivalent to between about 15 mg. and 50 mg. of rilpivirine.

In another embodiment, the combination or composition for use in the method comproses the administration of bictegravir is administered to the patient at about 5 mg, about 10 mg, about 25 mg, about 50 mg, about 75 mg, or about 100 mg, once, twice or three times a day. In another embodiment, bictegravir is administered to the patient at about 5 mg to 100 mg, at about 25 mg to 75 mg, at about 35 mg to 65 mg or about 45 mg to 55 mg, once or twice per day.

A further embodiment comprises a method of treating a virologically suppressed patient by switching the patient from a first antiretroviral regimen comprising a combination or composition that comprises at least three antiretroviral agents to a second antiviral regimen comprising a composition having only two antiretroviral agents being bictegravir and rilpivirine.

Still another embodiment comprises a method wherein the two antiretroviral agents are both present in a fixed dose combination.

Another embodiment comprises a method wherein one or both of the two antiretroviral agents of a combination or composition of the invention is/are taken with food, such as a food that comprises at least a moderate or higher fat content.

Another embodiment provides a method for preventing an HIV infection or AIDS, comprising administering to a human a therapeutically effective amount of bictegravir, or a pharmaceutically acceptable salt or form thereof; and a therapeutically effective amount of rilpivirine, or a pharmaceutically acceptable salt or form thereof.

In one embodiment there is a combination or composition of the invention for use in any of the methods described above.

DETAILED DESCRIPTION OF THE INVENTION

Bictegravir inhibits HIV integrase by binding to the integrase active site and blocking the strand transfer step of retroviral deoxyribonucleic acid ("DNA") integration which is essential for the HIV replication cycle. Strand transfer biochemical assays using purified HIV integrase and pre-processed substrate DNA resulted an IC50 values of 7.5 nM (Tsiang, M. et al., Antiviral Activity of Bictegravir (GS-9883), a Novel Potent HIV-1 Integrase Strand Transfer Inhibitor with an Improved Resistance Profile, *Antimicrobial Agents and Chemotherapy*, v.60: 12, 2016).

A chemical name of bictegravir is (2R,5S,13aR)-8-hidroxi-7,9-dioxo-N-[(2,4,6-trifluorofenil)metil]-2,3,4,5,7,9,13,13a-octahidro-2,5-metanopirido [1',2':4,5]pirazino[2,1-b][1,3]oxazepina-10-carboxamida. Certain regimens and compositions of the inventions comprise a pharmaceutically acceptable form of bictegravir, such as a pharmaceutically acceptable salt thereof. Bictegravir has the following structural formula of formula I:

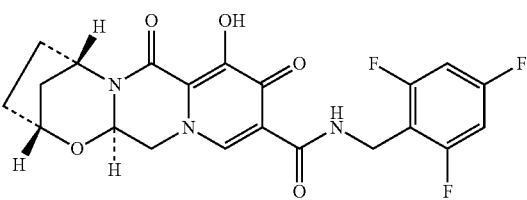

I

A method of making bictergravir is described in the patent U.S. Pat. No. 9,216,996.

Rilpivirine is a diarylpyrimidine non-nucleoside reverse transcriptase inhibitor (NNRTI) of human immunodeficiency virus type 1 (HIV-1) and inhibits HIV-1 replication by non-competitive inhibition of HIV-1 reverse transcriptase (RT). Rilpivirine does not inhibit the human cellular DNA polymerases $\alpha$, $\beta$ and $\gamma$.

A chemical name for rilpivirine is 4-[[4-[[4-[(E)-2-cyanoethenyl]-2,6-dimethylphenyl]amino]-2-pyrimidinyl]amino]benzonitrile. Certain regimens and compositions of the inventions comprise a pharmaceutically acceptable form of rilpivirine, such as a pharmaceutically acceptable salt thereof. Rilpivirine has the following structural formula of formula II:

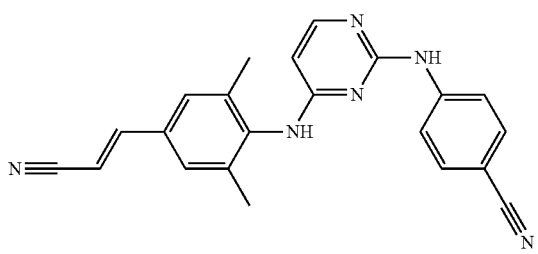

II

Rilpivirine is approved for use to treat HIV in tablet form. (See HIGHLIGHTS OF PRESCRIBING INFORMATION for EDURANT® rilpivirine tablets, 039310-150827, revised August 2015 (http://www.edurant.com/shared/prescribing-information-edurant.pdf), which is incorporated by reference herein in its entirety.

In one embodiment, this invention comprises a method of treating a patient infected with a human immunodeficiency virus using a combination or composition of the invention or using a regimen of the invention. For example the method provides administering to a patient infected with HIV a composition comprising bictegravir or a pharmaceutically acceptable salt thereof, and a composition comprising rilpivirine or a pharmaceutically acceptable salt thereof. Another embodiment comprises a method of treating a patient infected with Human Immunodeficiency Virus type 1 (HIV-1) or a mutant thereof, Human Immunodeficiency Virus type 2 (HIV-2) or a mutant thereof, or a virus that causes Acquired Immune Deficiency Syndrome (AIDS).

An embodiment of a regimen of the invention is provided that comprises switching to using a combination or composition of the invention from using a combination regimen comprising of three or more antiviral compounds selected from the group of: an anti-HIV agent, an HIV protease inhibitor, an HIV non-nucleoside or non-nucleotide inhibitor of reverse transcriptase, an HIV nucleoside or nucleotide inhibitor of reverse transcriptase, a n HIV integrase inhibitor, MK8591 (EFdA), bictegravir, a n HIV non-catalytic site (or allosteric) integrase inhibitor, an HIV entry inhibitor (e.g., a CCR5 inhibitor, a gp41 inhibitor (i.e., a fusion inhibitor) or a CD4 attachment inhibitor, a CXCR4 inhibitor, a gp120 inhibitor, a G6PD or an NADH-oxidase inhibitor, a latency reversing agent (e.g., a histone deacetylase inhibitor, a proteasome inhibitor, a protein kinase C (PKC) activator, o r a BRD4 inhibitor), a compound that targets HIV capsid (a "capsid inhibitor"; e.g., a capsid polymerization inhibitor or a capsid disrupting compound, a n HIV nucleocapsid p7 (NCp7) inhibitor, an HIV p24 capsid protein inhibitor), a pharmacokinetic enhancer, an immune-based therapy (e.g., a Pd-1 modulator, a Pd-L1 modulator, a CTLA4 modulator, an ICOS modulator, an OX40 modulator, a toll-like receptor modulator, an IL-15 agonist, an anti-HIV antibody, a bispecific antibody or an "antibody-like" therapeutic protein (e.g., a DART®, a DUOBODY®, aBITE®, anXmAb®, a TandAb®, aFab derivative) including those targeting a HIV gp120 or gp41, a combination drug for HIV, a n HIV p 17 matrix protein inhibitor, a n IL-13 antagonist, a peptidyl-prolyl cis-trans isomerase A modulator, a protein disulfide isomerase inhibitor, a complement C5a receptor antagonist, a DNA methyltransferase inhibitor, an HIV vif gene modulator, a Vif dimerization antagonist, an HIV-1 viral infectivity factor inhibitor, a TAT protein inhibitor, an HIV-1 Nef modulator, an Hck tyrosine kinase modulator, a mixed lineage kinase-3 (MLK-3) inhibitor, an HIV-1 splicing inhibitor, a Rev protein inhibitor, a n integrin antagonist, a nucleoprotein inhibitor, a splicing factor modulator, a COMM domain containing protein 1 modulator, an HIV ribonuclease H inhibitor, a retrorocyclin modulator, a CDK-9 inhibitor, a dendritic ICAM-3 grabbing nonintegrin 1 inhibitor, an HIV GAG protein inhibitor, an HIV POL protein inhibitor, a complement Factor H modulator, a ubiquitin ligase inhibitor, a deoxycytidine kinase inhibitor, a cyclin dependent kinase inhibitor, a proprotein convertase PC9 stimulator, an ATP-dependent RNA helicase DDX3X inhibitor, a reverse transcriptase priming complex inhibitor, an HIV gene therapy, a PI3K inhibitor, a compound, such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US 20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO 2014/100323 (Gilead Sciences), WO2012/145728 (Gilead Sciences), WO 2013/159064 (Gilead Sciences) and WO 2012/003498 (Gilead Sciences) and WO 2013/006792 (Pharma Resources), and other drugs for treating HIV. In a certain embodiment of such combination of antiviral drugs, the combination contains three antiretroviral drugs. Another embodiment of a regimen of the invention comprises switching from using a composition of the invention to using a composition comprising three of the aforementioned antiviral compounds. Another embodiment provides a method comprising switching to an antiretroviral regimen that comprises one INI and one antiretroviral agent selected from NNRTI or PI.

In another embodiment of such method the patient is virologically suppressed, such as having an HIV copy number of less than between 0 and 200 copies per mL, 20 copies per mL, 50 copies per mL, 100 copies per mL, or 200 copies per mL. Provided also as an embodiment for any copy number of the invention are each integer copy number between each end number of a copy number range. For example, a copy number range from 20 copies per mL to 50 copies per mL would also include 21, 22, 23 up to 49 copies per mL.

Also provided is an embodiment that is a regimen of the invention or composition of the invention administered to or used to treat an ART-experienced patient. A certain embodiment provides that this patient is also virologically suppressed.

Regimens of the invention and combinations and compositions of the invention are used to treat patients infected with a wild-type or mutant HIV or a virus comprising an HIV integrase homolog.

In another embodiment the human immunodeficiency virus in a patient is not resistant to either antiretroviral component of a composition of the invention, or is only partially resistant to either or both such antiretroviral component(s), or resistant to an integrase inhibitor, such as elvitegravir or raltegravir.

An embodiment of the invention also provides a combination or composition of the invention administered to a patient infected with wild-type HIV-1 or HIV-2, an HIV clade B virus, an HIV of M clade A, B, C, D, E, F, G or H, or an HIV group O virus.

An embodiment of the invention comprises a combination or composition of the invention used to treat a patient infected with a mutant HIV, such as an integrase inhibitor-resistant HIV, a raltegravir-resistant HIV, or an elvitegravir-resistant mutant.

An embodiment of a regimen of the invention provides administering a combination or composition of the invention to a patient infected with an NNRTI- or NNRTI-resistant strain that is sensitive to bictegravir or rilpivirine, such as a strain with an NNRTI substitutions, such as V90I, K101E/P/T, E138K/A/Q/G, V179I/L, Y181C/I, V189I, H221Y, F227C/L and M230L, an emtricitabine or lamivudine resistance-associated substitution M184I or V, or an NRTI resistance-associated substitution K65R/N, A62V, D67N/G, K70E, Y115F, T215S/T, or K219E/R.

Certain embodiments provide a method to administer a combination or composition of the invention to a treatment-experienced patient, such as a patient that is virologically-supressed. A further embodiment comprises a method of treating a virologically suppressed patient by switching the patient from a first antiretroviral regimen comprising a composition comprising at least three antiretroviral agents to second antiviral regimen comprising a combination or composition having only two antiretroviral agents being bictegravir and rilpivirine. In this embodiment, the antiviral regimens each may comprise any number of steps or undergo any number of manipulations and the compositions used in each regimen may comprise any number of components, such as excipients or biologically active compounds (e.g., non-antiviral pharmaceutical compounds); however, with regard to the number of antiviral agents in the first antiviral regimen and its composition that number is limited to three or more antiviral agents, but no fewer, and with regard to the number of antiviral agents in the second antiviral regimen and it composition that number is limited to two antiviral agents, no more nor fewer. For the avoidance of doubt, in a non-limiting example, a first regimen may have a composition containing four non-antiviral drugs, three antiviral drugs and twelve excipients and a second regimen may have a composition containing four non-antiviral drugs, two antiviral drugs (being bictegravir and rilpivirine) and twelve excipients. In some embodiments, the compositions may comprise antiviral agents and non-antiviral agents. One embodiment of the invention comprises a first antiviral regimen comprising an integrase inhibitor, for example, elvitegravir or raltegarvir, or a composition comprising bictegravir, emtricitibine, and tenofovir alafenamide ("TAF") (e.g., bictegravir (50 mg.), emtricitabine (200 mg.), and TAF (25 mg.)).

An embodiment of a regimen of the invention provides administering a composition of the invention to a patient infected with a certain mutant HIV-1 virus, such as a mutant virus comprising a single amino acid substitution or two or more substitutions. Certain of such regimens provide administering a composition of the invention to a patient infected with an INSTI substitution mutant, such as an INSTI-resistant mutant, a raltegravir-resistant mutant, an elvitegravir-resistant mutant, or a an HIV-1 mutant comprising an NNRTI-resistant substitution, an NRTI-resistant substitution, or a PI-resistant substitution.

Other embodiments provide methods of administering a combination or composition of the invention to a human infected with an HIV-2 mutant.

An embodiment of a regimen of the invention provides administering a combination or composition of the invention to a human infected with certain mutant HIV viruses showing a decrease in antiviral activity to a reverse transcriptase inhihitor.

Still another embodiment provides a regimen of the invention administered to a patient infected with HIV comprising an INSTI substitution.

Any embodiment of the invention that comprises or relates to a patient also comprises or relates to a human. Any combination or composition of the invention can be administered to a human. Any regimen of the invention can be used on a human, for example to treat a human, such as a human infected with HIV or with AIDS.

Another embodiment provides a method for preventing an HIV infection or AIDS, comprising administering to a human a therapeutically effective amount of bictegravir, or a pharmaceutically acceptable salt thereof and a therapeutically effective amount of rilpivirine, or a pharmaceutically acceptable salt thereof to a patient who is at risk of acquiring HIV infection. For example, this method is used as a prophylactic for an intravenous drug abuser, a person who contacts or has a likelihood of contacting bodily fluid from an HIV-infected individual, or a person who engages or may engage in a sexual or other activity associated with a risk of acquiring an HIV infection.

A certain regimen of the invention provides dosing with bictegravir or a pharmaceutically acceptable form or salt thereof and rilpivirine or a pharmaceutically acceptable form or salt thereof to a patient simultaneously in a composition comprising both antiviral agents, or alternatively with each agent in separate compositions, or a combination of such compositions. In another embodiment, such compositions are either in liquid form or solid form or another form (e.g. a gel, sol, or emulsion) or a combination of such forms suited to any of various routes of administration to a patient. In certain embodiments a method of treatment comprises two antiviral agents (e.g., bictegravir and rilpivirine) each taken once daily, and each agent may be taken orally. A composition of the invention comprising bictegravir and rilpivirine may be ingested as one or more tablets taken orally. Still another embodiment comprises a method wherein the two antiretroviral agents are both present in a fixed dose combination. An additional embodiment provides taking one or more of such compositions once, twice, three times daily or more, depending on the dose that is therapeutically effective for a given patient. Certain regimens provide that a composition of the invention be taken with food, such as a meal. Also provided is a regimen wherein the meal comprises fat.

An embodiment of the invention provides a therapeutically effective regimen of the invention or a therapeutically effective composition of the invention.

A further embodiment of the invention provides a combination or composition for use in the regimens of the invention comprising a pharmaceutically acceptable form of bictegravir such as bictegravir sodium or other pharmaceutically acceptable salt equivalent to between about 40 mg. and 200 mg. of bictegravir and a pharmaceutically acceptable form of rilpivirine such as rilpivirine hydrochloride equivalent to between about 15 mg. and 75 mg. of rilpivirine. Yet another embodiment comprises such equivalents of 50 mg., 75 mg., 100 mg., 150 mg., or 200 mg. of bictegravir; and 25 mg., 30 mg., or 50 mg. of rilpivirine. In a further embodiment a tablet or other composition may comprise a pharmaceutically acceptable form of bictegravir equivalent to 100 mg. or 75 mg. of bictegravir free acid and comprise a pharmaceutically acceptable form of rilpivirine equivalent to 25 mg. of rilpivirine free base. Provided as an embodiment for any dose range of the invention is each integer dose amount between each end number of a dose range. For example, a dose range from 15 mg. to 50 mg. would also include 16 mg., 17 mg., and so on up to 49 mg. Other therapeutically effective doses of bictegravir and rilpivirine can be determined or optimized using known pharmaceutical or clinical practices.

Another embodiment provides a composition of the invention of the invention further comprising one or more pharmaceutically acceptable excipients. Pharmaceutically acceptable excipients for various different dosage forms are well-known in the art and include carriers, diluents, fillers, binders, lubricants, disintegrants, glidants, colorants, pigments, taste masking agents, sweeteners, flavorants, plasticizers, and any acceptable auxiliary substances such as absorption enhancers, penetration enhancers, surfactants, co-surfactants, and specialized oils. The proper excipient(s) is (are) selected based in part on the dosage form, the intended mode of administration, the intended release rate, and manufacturing reliability. Examples of common types of excipients include various polymers, waxes, calcium phosphates, sugars, among others.

Other embodiments comprise pharmaceutical compositions formulated into various types of dosage forms, for example as solutions or suspensions, or as tablets, capsules, granules, pellets or sachets for oral administration. One embodiment of a pharmaceutical composition is in the form of a solid oral dosage form. In another embdiment a dosage form is a tablets, such as a swallowable tablet. In a further embodiment it is coated with a film coat comprising, for example, any suitable inert coating material known in the art. The above lists of excipients and forms are not exhaustive.

A pharmaceutical composition of the present invention can be manufactured according to standard methods known in the art. Granulates according to the invention can be obtained by dry compaction or wet granulation. These granulates can subsequently be mixed with a number of agents known in the art, such as suitable disintegrating agents, glidants and lubricants and the mixture can be compressed into tablets or filled into sachets or capsules of suitable size. Tablets can also be obtained by direct compression of a suitable powder mixture, i.e. without any preceding granulation of the excipients.

Suitable powder or granulate mixtures according to the invention are also obtainable by spray drying, lyophilization, melt extrusion, pellet layering, coating of the active pharmaceutical ingredient or any other suitable method. The obtained powders or granulates can be mixed with one or more suitable ingredients and the resulting mixtures can either be compressed to form tablets or filled into sachets or capsules. The above mentioned methods known in the art also include grinding and sieving techniques permitting the adjustment of desired particle size distributions.

As a further embodiment, a composition comprising bictegravir or rilpivirinecan be formulated for parenteral administration, such as through intravenous administration of one or both of a composition comprising bictegravir or a composition comprising rilpivirine. Also provided is an embodiment comprising a solid (e.g., a nanoparticulate composition), solution, or liquid formulation for parenteral administration. Parenteral administration can be performed using a suitable device, a number of which are known.

The composition according to the present invention may be used as medicament or be used in making a medicament. It may be supplied in packs or kits.

In some circumstances, certain patients may be tested to assess a degree of renal impairment or skin or tissue disorders. An embodiment of the invention provides testing a bodily sample to detect such impairment or disorders in patients being administered a composition of the invention.

In a patient co-infected with hepatitis C or hepatitis B and HIV who is determined to have a higher incidence of liver chemistry elevations (grade 1) observed compared to those who were not co-infected with either hepatitis virus, an embodiment provides a method whereby a test is performed to detect HIV infection and hepatitis C infection and/or hepatitis B infection, either prior to or during use of a regimen or compositon of the invention.

A further embodiment provides a method of discontinuing the use of a composition of the invention where a patient develops a rash, atopic dermatitis, or diarrhea following administration of such composition.

Bictegravir is metabolically cleared through certain actions of CYP3A4 and UGT1A1. In vitro studies revealed that bictegravir is a substrate of UGT1A3, UGT1A9, BCRP, and P-gp. Therefore, certain drug-drug interactions may occur. (Gallant, J. et al. Antiviral Activity, Safety, and Pharmacokinetics of Bictegravir as 10-Day Monotherapy in HIV-1—Infected Adults, *Clinical Science*, v.75: 1, May 1, 2017.)

Rilpivirine is primarily metabolized by CYP3A, and drugs that induce or inhibit CYP3A may thus affect the clearance of rilpivirine. Co-administration of a composition of the invention and drugs that induce CYP3A may result in decreased plasma concentrations of rilpivirine and loss of virologic response and possible resistance to rilpivirine or to the relevant class of NNRTIs. Co-administration of a composition of the invention and drugs that inhibit CYP3A may result in increased plasma concentrations of rilpivirine.

Co-administration of a composition of the invention with drugs that increase gastric pH may result in decreased plasma concentrations of rilpivirine and loss of virologic response and possible resistance to rilpivirine or to the relevant class of NNRTIs. Rilpivirine 25 mg. once daily is not likely to have a clinically relevant effect on the exposure of medicinal products metabolized by CYP enzymes.

Information regarding potential drug-drug interactions with bictegravir, rilpivirine or a composition of the invention are provided in Table 1 and Table 2. A composition of the invention is not co-administered with other HIV antiviral agents and certain information is provided for reference or to indicate drug-drug interactions to be avoided.

The pharmacokinetic properties of rilpivirine have been evaluated in adult healthy subjects and in adult antiretroviral treatment-naive HIV-1-infected subjects. Exposure to rilpivirine was generally lower in HIV-1 infected subjects than in healthy subjects.

An embodiment of the invention is a regimen wherein a composition that comprises bictegravir, or a pharmaceutically acceptable form thereof, is used at a higher or lower dose or is administered more or less frequently when one or more of the compounds in Table 1 or Table 2 is administered to a patient as compared to when none of such compounds are administered to a patient.

TABLE 1

Embodiments of dosages of a composition of the invention co-administered with certain other compositions.

| Concomitant Drug Class: Drug Name | Effect on Concentration | Exemplary Embodiment |
|---|---|---|
| HIV-1 Antiviral Agents | | |
| Non-nucleoside Reverse Transcriptase Inhibitors: Delavirdine, Efavirenz, Etravirine, Nevirapine | ↓Bictegravir ↓Rilpivirine (↑ with delavirdine) | No coadministration of a composition of the invention with another NNRTI. |
| Protease Inhibitor: Tipranavir/ritonavir | ↓Bictegravir ↑Rilpivirine | No coadministration of a composition of the invention with tipranavir/ritonavir. |
| Other Agents | | |
| Clarithromycin Erythromycin Telithromycin | ↔Bictegravir ↑Rilpivirine | No dose adjustment. Consider an alternative agent, such as azithromycin. |
| Antacids containing aluminum, magnesium hydroxide, and/or calcium carbonate): Cation-containing antacids[b] or laxatives Sucralfate Buffered medications | ↓Bictegravir ↓Rilpivirine | Administer a composition of the invention about 4 hours before or about 6 hours after taking one or more antacids. |
| Oral calcium and iron supplements, such as multivitamins containing calcium or iron (non-antacid) | ↓Bictegravir | Administer a composition of the invention about 4 hours before or about 6 hours after taking one or more supplements comprising calcium or iron. Alternatively, a composition of the invention and supplements comprising calcium or iron can be taken together, for example with food. |
| H$_2$-Receptor Antagonists: Famotidine Cimetidine Nizatidine Ranitidine | ↔Bictegravir ↓Rilpivirine | A composition of the invention administered at least 12 hours after or at least 4 hours before an H$_2$-receptor antagonists. |
| Metformin[b] | ↑Metformin | With concomitant use, limit the total daily dose of metformin to 1,000 mg either when starting metformin or a composition of the invention. When starting or stopping a composition of the invention, the metformin dose may require an adjustment, such as per a physician's instruction. Monitoring of blood glucose when initiating concomitant use and after withdrawal of a composition of the invention. |
| Methadone | ↔Bictegravir ↔Methadone ↔Rilpivirine | No dose adjustments are required when starting coadministered of methadone with a composition of the invention. However, clinical monitoring is recommended as methadone maintenance therapy may need to be adjusted in some patients. |

TABLE 1-continued

Embodiments of dosages of a composition of the invention co-administered with certain other compositions.

| Concomitant Drug Class: Drug Name | Effect on Concentration | Exemplary Embodiment |
|---|---|---|
| Rifabutin | ↔Bictegravir ↔Rifabutin ↓Rilpivirine | Adjust rilpivirine dose to 50 mg. once daily when rifabutin is coadministered. An additional 25 mg. dose of rilpivirine should be taken with a composition of the invention while rifabutin is coadministered. |

TABLE 2

Further embodiments of dosages of a composition of the invention co-administered with certain other compositions.

| Coadministered Drug(s) and Dose(s) | Dose of Bictegravir |
|---|---|
| Daclatasvir 60 mg once daily | Between 50 mg and 125 mg. once daily |
| Ethinyl estradiol 0.035 mg | Between 50 mg and 125 mg. twice daily |
| Metformin 500 mg twice daily | Between 50 mg and 125 mg. once daily |
| Metformin 500 mg twice daily | Between 50 mg and 125 mg. twice daily |
| Methadone 16 mg to 150 mg | Between 50 mg and 125 mg. twice daily |
| Midazolam 3 mg | Between 25 mg. and 50 mg. once daily |
| Norelgestromin 0.25 mg | Between 50 mg and 125 mg. twice daily |
| Rilpivirine 25 mg once daily | Between 50 mg and 125 mg. once daily |
| Tenofovir disoproxil fumarate 300 mg once daily | Between 50 mg and 125 mg. once daily |
| Atazanavir 400 mg once daily | Between 20 mg. and 70 mg. once daily |
| Atazanavir/ritonavir 300 mg/100 mg once daily | Between 20 mg. and 70 mg. once daily |
| Darunavir/ritonavir 600 mg/100 mg twice daily | Between 40 mg. and 70 mg. once daily |
| Efavirenz 600 mg once daily | Between 50 mg and 125 mg. once daily |
| Etravirine 200 mg twice daily | Between 50 mg and 125 mg. once daily |
| Etravirine + darunavir/ritonavir 200 mg + 600 mg/100 mg twice daily | Between 50 mg and 125 mg. once daily |
| Etravirine + lopinavir/ritonavir 200 mg + 400 mg/100 mg twice daily | Between 40 mg. and 70 mg. once daily |
| Fosamprenavir/ritonavir 700 mg/100 mg twice daily | Between 40 mg. and 70 mg. once daily |
| Lopinavir/ritonavir 400 mg/100 mg twice daily | Between 40 mg. and 70 mg. once daily |
| Rilpivirine 25 mg once daily | Between 50 mg and 125 mg. once daily |
| Tenofovir 300 mg once daily | Between 50 mg and 125 mg. once daily |
| Tipranavir/ritonavir 500 mg/200 mg twice daily | Between 50 mg and 125 mg. once daily |
| Antacid (e.g., Maalox ®) simultaneous administration | Between 50 mg and 125 mg. once daily |
| Antacid (e.g., Maalox ®) About 2 hours after bictegravir | Between 50 mg and 125 mg. once daily |
| Boceprevir 800 mg every 8 hours | Between 50 mg and 125 mg. once daily |
| Calcium carbonate 1,200 mg simultaneous administration (fasted) | Between 50 mg and 125 mg. once daily |
| Calcium carbonate 1,200 mg simultaneous administration (fed) | Between 50 mg and 125 mg. once daily |
| Calcium carbonate 1,200 mg About 2 h after bictegravir | Between 50 mg and 125 mg. once daily |
| Carbamazepine 300 mg twice daily | Between 50 mg and 125 mg. once daily |
| Daclatasvir 60 mg once daily | Between 50 mg and 125 mg. once daily |
| Ferrous fumarate 324 mg simultaneous administration (fasted) | Between 50 mg and 125 mg. once daily |
| Ferrous fumarate 324 mg simultaneous administration (fed) | Between 50 mg and 125 mg. once daily |
| Ferrous fumarate 324 mg About 2 h after bictegravir | Between 50 mg and 125 mg. once daily |
| Multivitamin (e.g., One-A-Day ®) simultaneous administration | Between 50 mg and 125 mg. once daily |
| Omeprazole 40 mg once daily | Between 50 mg and 125 mg. once daily |
| Prednisone 60 mg once daily with taper | Between 50 mg and 125 mg. once daily |
| Rifampin 600 mg once daily | Between 20 mg and 125 mg. twice daily |
| Rifampin 600 mg once daily | Between 20 mg and 125 mg. twice daily |
| Rifabutin 300 mg once daily | Between 50 mg and 125 mg. once daily |
| Daclatasvir 60 mg once daily | Between 50 mg and 125 mg. once daily |
| Ethinyl estradiol 0.035 mg | Between 50 mg and 125 mg. twice daily |
| Metformin 500 mg twice daily | Between 50 mg and 125 mg. once daily |
| Metformin 500 mg twice daily | Between 50 mg and 125 mg. twice daily |
| Methadone 16 to 150 mg | Between 50 mg and 125 mg. twice daily |
| Midazolam 3 mg | Between 25 mg. and 50 mg. once daily |
| Norelgestromin 0.25 mg | Between 50 mg and 125 mg. twice daily |
| Rilpivirine 25 mg once daily | Between 50 mg and 125 mg. once daily |
| Tenofovir disoproxil fumarate 300 mg once daily | Between 50 mg and 125 mg. once daily |

Under certain circumstances any information provided herein or derived herefrom that relates to regimen of the invention or composition of the invention may be included in a product label. Such circumstances may include, for example, requirements of a regulatory body, outcomes or data from clinical studies, or a decision of a manufacturer or other company.

Any patent application to which this application claims priority is incorporated by reference herein in its entirety.

What is claimed is:

1. A method of treating a patient infected with a human immunodeficiency virus using only two antiretroviral agents comprising administering a composition comprising bictegravir or a pharmaceutically acceptable salt thereof and a composition comprising rilpivirine or a pharmaceutically acceptable salt thereof.

2. The method of claim 1 wherein the patient is virologically suppressed having an HIV copy number of less than 50 copies per mL.

3. The method of claim 1 wherein the human immunodeficiency virus is not resistant to either antiretroviral component.

4. The method of claim 1 wherein the human immunodeficiency virus is partially resistant to either antiretroviral component.

5. The method of treatment of claim 1 wherein the two antiviral agents are each taken once daily.

6. The method of treatment of claim 1 wherein the two antiviral agents are each taken orally.

7. The method of claim 1 wherein the pharmaceutically acceptable bictegravir is bictegravir sodium equivalent to 75 mg of bictegravir and the pharmaceutically acceptable rilpivirine is rilpivirine hydrochloride equivalent to 25 mg of rilpivirine.

8. A method of treating a virologically suppressed patient having an HIV copy number of less than 50 copies per mL by switching the patient from an antiretroviral regimen comprising at least three antiretroviral agents to a regimen comprising only the two antiretroviral agents being bictegravir and rilpivirine.

9. The method of claim 8 wherein the first antiretroviral regimen comprises one INI and two or more of antiretroviral agent selected from an NRT, an NNRTI, or a PI.

10. The method of claim 1 wherein the two antiretroviral agents are both present in a fixed dose combination.

11. The method of claim 1 wherein one or both of the two antiretroviral agents is taken with food.

12. The method of claim 1 wherein the food comprises at least a moderate or higher fat content.

* * * * *